US008909492B2

(12) United States Patent
McKeon (10) Patent No.: US 8,909,492 B2
(45) Date of Patent: Dec. 9, 2014

(54) ULTRASONIC INSPECTION USING ACOUSTIC MODELING (75) Inventor: James C. P. McKeon, Woodbridge, VA (US)

(73) Assignee: Sonix, Inc., Springfield, VA (US)

( * ) Notice: Subject to any disclaimer, the term of this patent is extended or adjusted under 35 U.S.C. 154(b) by 963 days.

(21) Appl. No.: 13/031,340

(22) Filed: Feb. 21, 2011

(65) Prior Publication Data

US 2011/0144935 A1    Jun. 16, 2011

Related U.S. Application Data (62) Division of application No. 11/482,347, filed on Jul. 7, 2006, now Pat. No. 7,917,317.

(51) Int. Cl.
G01R 13/00 (2006.01)
G01N 29/04 (2006.01)
G01N 29/44 (2006.01)

(52) U.S. Cl.
CPC ........ G01N 29/043 (2013.01); G01N 2291/101 (2013.01); G01N 2291/044 (2013.01); G01N 29/4418 (2013.01); G01N 2291/02854 (2013.01); G01N 29/4472 (2013.01)
USPC .......................................................... 702/66

(58) Field of Classification Search
CPC combination set(s) only.
See application file for complete search history.

(56) References Cited

U.S. PATENT DOCUMENTS

| 3,063,290 A | 11/1962 | Kaserman et al. |
| 3,284,795 A | 11/1966 | Fertig et al. |
| 3,489,608 A | 1/1970 | Jacobs et al. |
| 3,558,093 A | 1/1971 | Bok |
| 3,617,045 A | 11/1971 | DaCosta et al. |
| 3,678,735 A | 7/1972 | Boulanger et al. |
| 3,737,573 A | 6/1973 | Kessler |
| 3,760,822 A | 9/1973 | Evans |
| 3,765,431 A | 10/1973 | Jannett et al. |
| 3,790,281 A | 2/1974 | Kessler et al. |
| 3,850,025 A | 11/1974 | Nakanishi et al. |
| 3,850,027 A | 11/1974 | Nakanishi et al. |
| 3,886,793 A | 6/1975 | Cramer et al. |
| 3,898,839 A | 8/1975 | White |
| 3,988,196 A | 10/1976 | Wanesky |
| 4,008,602 A | 2/1977 | Love |
| 4,012,951 A | 3/1977 | Kessler |
| 4,058,000 A | 11/1977 | Ries et al. |
| 4,093,378 A | 6/1978 | Horr et al. |
| 4,164,150 A | 8/1979 | Ries et al. |
| 4,208,915 A | 6/1980 | Edwards |

(Continued)

OTHER PUBLICATIONS

Letter dated Feb. 12, 1997 from Sonix to Hewlett Packard.

Primary Examiner — Elias Desta (57) ABSTRACT

Configuration of an ultrasonic inspection system is facilitated using an ultrasound response predicted by a simulation tool. In one embodiment, estimated material properties of an object to be inspected are input to the simulation tool. Also input to the simulation tool is at least one estimated property of an ultrasonic transducer of the ultrasonic inspection. The simulation tool predicts the response of the object to ultrasound from the ultrasonic transducer. This response is dependent upon the estimated material properties of the object to be inspected and the at least one estimated property of the ultrasonic transducer. The ultrasonic inspection system is then configured dependent upon a feature of the predicted response. The system may be configured, for example, by setting the position of a time gate, selecting an appropriate ultrasonic transducer, selecting the position of the transducer to achieve good focus, or selecting parameters for signal processing.

16 Claims, 12 Drawing Sheets

(56) References Cited

U.S. PATENT DOCUMENTS

| | | |
|---|---|---|
| 4,238,962 A | 12/1980 | Taenzer |
| 4,252,125 A | 2/1981 | Iinuma |
| 4,316,271 A | 2/1982 | Evert |
| 4,332,016 A | 5/1982 | Berntsen |
| 4,344,448 A | 8/1982 | Potts |
| 4,472,975 A | 9/1984 | Beck et al. |
| 4,517,985 A | 5/1985 | Teslawski et al. |
| 4,518,992 A | 5/1985 | Kessler et al. |
| 4,526,038 A | 7/1985 | Box et al. |
| 4,543,130 A | 9/1985 | Shwartzman |
| 4,662,215 A | 5/1987 | Eckert |
| 4,781,067 A | 11/1988 | Cichanski |
| 4,807,634 A | 2/1989 | Enjoji et al. |
| 4,852,397 A | 8/1989 | Haggag |
| 4,854,337 A | 8/1989 | Bunkenburg et al. |
| 4,866,986 A | 9/1989 | Cichanski |
| 4,867,168 A | 9/1989 | Stoor et al. |
| 4,920,803 A | 5/1990 | Karaki et al. |
| 4,924,707 A | 5/1990 | Kliesch |
| 4,977,779 A | 12/1990 | Karaki et al. |
| 5,014,711 A | 5/1991 | Nagasaki |
| 5,060,517 A | 10/1991 | Fushimi et al. |
| 5,077,695 A | 12/1991 | Khuri-yakub et al. |
| 5,117,697 A | 6/1992 | Takishita et al. |
| 5,195,729 A | 3/1993 | Thomas et al. |
| 5,212,987 A | 5/1993 | Dransfeld et al. |
| 5,240,522 A | 8/1993 | Tanaka et al. |
| 5,301,552 A | 4/1994 | Nagura et al. |
| 5,320,225 A | 6/1994 | Kirkpatrick |
| 5,337,611 A | 8/1994 | Fleming et al. |
| 5,359,895 A | 11/1994 | Isenberg et al. |
| 5,374,021 A | 12/1994 | Kleinman |
| 5,374,829 A | 12/1994 | Sakamoto et al. |
| 5,431,054 A | 7/1995 | Reeves et al. |
| 5,469,742 A | 11/1995 | Lee et al. |
| 5,531,119 A | 7/1996 | Meyers |
| 5,549,003 A | 8/1996 | Drescher-Krasicka |
| 5,585,564 A | 12/1996 | Brunty et al. |
| 5,600,068 A | 2/1997 | Kessler et al. |
| 5,629,865 A | 5/1997 | Roth |
| 5,646,351 A | 7/1997 | Good et al. |
| 5,668,452 A | 9/1997 | Villarreal et al. |
| 5,684,252 A | 11/1997 | Kessler et al. |
| 5,874,319 A | 2/1999 | Dunaway et al. |
| 5,922,961 A | 7/1999 | Hsu et al. |
| 5,948,985 A | 9/1999 | Brautigan et al. |
| 5,996,415 A | 12/1999 | Stanke et al. |
| 6,027,605 A | 2/2000 | Lehmann et al. |
| 6,044,705 A | 4/2000 | Neukermans et al. |
| 6,062,084 A | 5/2000 | Chang et al. |
| 6,085,591 A | 7/2000 | Mallard |
| 6,089,095 A | 7/2000 | Yang et al. |
| 6,156,921 A | 12/2000 | Nance et al. |
| 6,227,946 B1 | 5/2001 | Gonzales-Martin et al. |
| 6,230,896 B1 | 5/2001 | Lambert |
| 6,261,370 B1 | 7/2001 | Otsuki et al. |
| 6,357,136 B1 | 3/2002 | Erickson et al. |
| 6,460,414 B1 | 10/2002 | Erickson et al. |
| 6,513,796 B2 | 2/2003 | Leidy et al. |
| 6,524,351 B2 | 2/2003 | Ohta |
| 6,540,014 B2 | 4/2003 | Getchel et al. |
| 6,554,003 B1 | 4/2003 | Birang et al. |
| 6,603,103 B1 | 8/2003 | Ulrich et al. |
| 6,709,877 B2 | 3/2004 | Tsui et al. |
| 6,710,886 B2 | 3/2004 | Park et al. |
| 6,712,765 B2 | 3/2004 | Glenn |
| 6,743,296 B2 | 6/2004 | Kao |
| 6,865,509 B1 | 3/2005 | Hsiung et al. |
| 6,880,387 B2 | 4/2005 | Kessler et al. |
| 6,890,302 B2 | 5/2005 | Oravez et al. |
| 6,895,820 B2 | 5/2005 | Oravez et al. |
| 6,912,908 B2 | 7/2005 | Kessler et al. |
| 6,921,672 B2 | 7/2005 | Satya et al. |
| 6,925,882 B1 | 8/2005 | Fleming et al. |
| 6,981,417 B1 | 1/2006 | Oravez et al. |
| 7,000,475 B2 | 2/2006 | Oravez et al. |
| 7,013,732 B2 | 3/2006 | McKeon |
| 7,079,975 B1 | 7/2006 | Halliyal et al. |
| 7,100,449 B2 | 9/2006 | Busch et al. |
| 7,131,333 B2 | 11/2006 | Busch |
| 7,181,969 B2 | 2/2007 | Busch et al. |
| 7,284,769 B2 * | 10/2007 | Breed ............... 280/735 |
| 7,286,964 B2 | 10/2007 | Kim |
| 7,590,510 B2 | 9/2009 | Kim |
| 2005/0257617 A1 | 11/2005 | Busch et al. |
| 2005/0286044 A1 | 12/2005 | Huibers |
| 2006/0081051 A1 | 4/2006 | Kessler |
| 2007/0012115 A1 | 1/2007 | Busch et al. |
| 2007/0180914 A1 | 8/2007 | Kessler |
| 2008/0006091 A1 | 1/2008 | McKeon |

* cited by examiner

ULTRASONIC INSPECTION USING ACOUSTIC MODELING

PRIORITY CLAIM

This application is a divisional application of application Ser. No. 11/482,347 filed on Jul. 7, 2006, now U.S. Pat. No. 7,917,317, the entire disclosure of which is incorporated into this application by reference and to which the instant application claims priority.

BACKGROUND

The performance of an ultrasonic inspection system is dependent upon many factors. These factors include, for example, the type of ultrasonic transducer used and the positioning of the ultrasonic transducer relative to the object under inspection. For optimal performance these factors need to selected dependent upon the physical characteristics of the object under inspection. However, the user of an ultrasonic inspection system often does not have sufficient expertise to make good selections. Consequently, the quality of the relating inspection is degraded compared to the optimal performance of the inspection system.

One approach is for the manufacturer of an ultrasonic inspection system to provide a list of commonly used configurations that can be accessed by the user. However this approach does not help the user when an object with a different structure is to be inspected. Further, this approach does not assist the user in developing an understanding of the capabilities of the inspection system.

BRIEF DESCRIPTION OF THE DRAWINGS

The novel features believed characteristic of the invention are set forth in the appended claims. The invention itself, however, as well as the preferred mode of use, and further objects and advantages thereof, will best be understood by reference to the following detailed description of an illustrative embodiment when read in conjunction with the accompanying drawing(s), wherein:

DETAILED DESCRIPTION

While this invention is susceptible of embodiment in many different forms, there is shown in the drawings and will herein be described in detail one or more specific embodiments, with the understanding that the present disclosure is to be considered as exemplary of the principles of the invention and not intended to limit the invention to the specific embodiments shown and described. In the description below, like reference numerals are used to describe the same, similar or corresponding parts in the several views of the drawings.

The performance of an ultrasonic inspection system can be degraded by a number of factors. An ultrasonic inspection system operating in a reflection mode, for example, relies upon reflection of ultrasonic from impedance mismatches in the object under inspection. These mismatches may be due to layers of material with different acoustic properties or to defects, such as voids, in the object. An object such as a semiconductor chip, a silicon wafer or a micro-machined device, may have many material layers. Consequently, multiple reflections are generated when an ultrasonic pulse is incident upon the object. One technique for isolating a particular reflection is to apply a time gate to the sensed reflection signal. The time gate removes portions of the signal outside of a selected time region. If the region is selected incorrectly, or if multiple reflections are present in the selected time region, the inspection image will be degraded.

The performance may also be degraded by poor focus of the ultrasonic beam from the transducer. In many applications, water is used to couple ultrasound from the transducer to the object under inspection. Commonly, the focal length of the transducer in water is specified. However, the focal length will be changed when the beam passes through the object. This change in focal length is determined by the detailed structure of the material layers of the object. The focal point may be adjusted to a certain degree by adjusting the relative positions of the object and the transducer, but physical limitations may even prevent good focus from being achieved. Perfect focus cannot usually be achieved, resulting in a finite 'beam spot size', that relates to the minimum beam width in the object.

Signal processing techniques may be used to enhance the quality of the inspection. Some of these processing techniques rely on assumptions about the received reflection signal.

One aspect of the present invention relates to method for configuring an ultrasonic inspection system. In one embodiment, estimated material properties of an object to be inspected are input to a simulation tool. Also input to the simulation tool is at least one estimated property of an ultrasonic transducer of the ultrasonic inspection system. The simulation tool predicts the response of the object to ultrasound from the ultrasonic transducer. This response is dependent upon the estimated material properties of the object to be inspected and the at least one estimated property of the ultrasonic transducer. The ultrasonic inspection system is then configured dependent upon a feature of the predicted response. The system may be configured, for example, by setting the position of a time gate, selecting an appropriate ultrasonic transducer, selecting the position of the transducer to achieve good focus, or selecting parameters for signal processing.

It is known that the scattering of acoustic waves from layered materials can be predicted if the properties of the materials, such as the density, sound speed and thickness of the layers, are known. The sound speed and layer thickness may be used to determine propagation time, while the density and sound speed (or equivalently the acoustic impedance) may be used to determine the reflection and refraction properties of an interface. The scattered wave may be the result of an incident ultrasonic wave being reflected from object or transmitted through the object. The scattered wave may also be the result of a sound source within the object. In many applications of ultrasonic inspection the material properties are known, at least approximately, before an inspection is made. Consistent with one embodiment of the invention, the user of an ultrasonic inspection system is provided with a software tool that takes material properties of an object under inspection as inputs and produces a display of a wave that is predicted to be scattered from the object. The tool uses an acoustic model of the object to predict the scattered wave from a given incident pulse.

In a further embodiment, the software tool is used to predict the path of the ultrasonic beam through the object. This tool may predict, for example, the focal point of the beam and the spot size of the beam.

Figure 1:
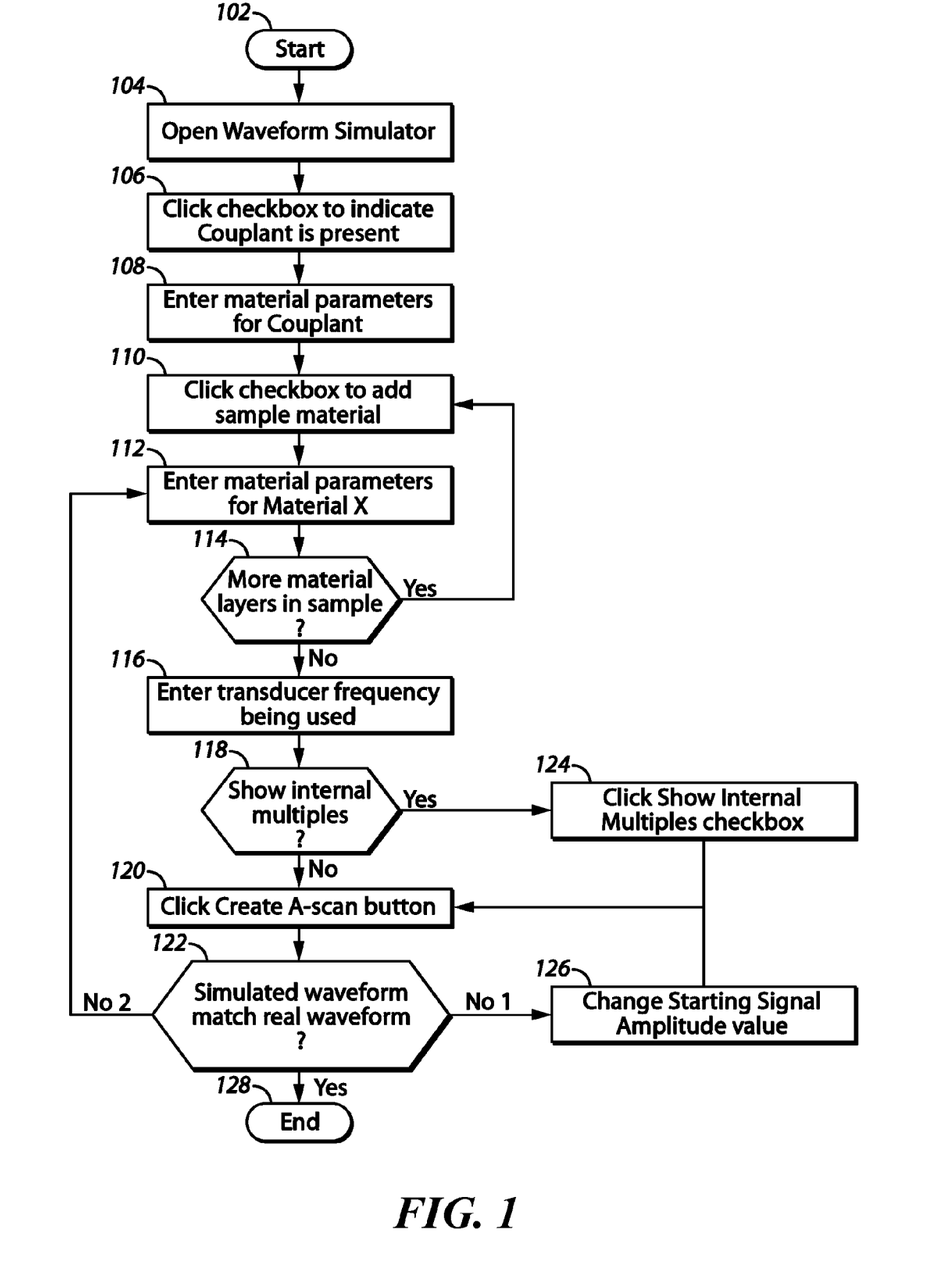
FIG. 1 is a flow chart of a method for acoustic modeling, consistent with certain embodiments of the invention.

FIG. 1 is a flow chart of an exemplary method consistent with certain embodiments of the invention. The method allows a user to model the scattering (transmission and/or reflection) of an ultrasonic pulse in an object under inspection. Following start block 102 in FIG. 1 a wave simulator tool is started at block 104. The wave simulator tool presents a user interface to the user. At 106 the user clicks a checkbox on the user interface if a coupling medium (couplant) is present between the ultrasonic transducer and the object. If a coupling medium is present, the user enters material properties for the coupling medium at block 108. At block 110 the user clicks a checkbox on the user interface to add a layer of sample material to the model of the object under inspection. At block 112 the user enters material properties, such as thickness, density and wave speed, for the new layer. Layer dimensions may also be entered. If more layers are to be entered, as depicted by the positive branch from decision block 114, flow returns to block 110 to allow properties of the additional layers to be added. This process continues until the properties of all layers of the object have been entered, as depicted by the negative branch from decision block 114. At block 116, the user enters the properties of the transducer being used. These properties may be retrieved from a database indexed by transducer type. The properties may include the frequency of the transducer, the shape of the transducer and/or the shape of the sound emitting surface of the transducer. If the user does not wish for internal multiple reflections to be displayed, as depicted by the negative branch from decision block 118, the user clicks a button to create a predicted A-scan (a display of amplitude versus time) at block 120. Further description of the creation of the A-scan is provided below with reference to FIG. 2. The predicted A-scan may then be compared with an actual A-scan from the object. If the predicted and actual A-scans match sufficiently well, as depicted by the positive branch from decision block 122, the process terminates at block 128. If the predicted and actual A-scans do not match sufficiently well, as depicted by the negative branch from decision block 122, flow returns to block 112 and the material properties may be adjusted to improve the match.

The match may be improved, for example, by selecting the positive branch from decision block 118, indicating that the user wishes to display internal multiple reflections. The user then clicks a checkbox at block 124 to indicate that internal multiple reflections are to be displayed and flow continues to block 120. The simulation tool than includes multiple reflections in the computation of the predicted A-scan waveform. As depicted by branch 1 from decision block 122, the amplitude of the incident wave pulse may be adjusted at block 126 and flow continues to block 120. Alternatively, as depicted by branch 2 from decision block 122, flow returns to block 112 to allow adjustment the material properties of one or more layers.

In one embodiment of the invention, the model is adjusted by the user.

In a further embodiment, the material properties are adjusted automatically by the simulation tool. Using a measure of mismatch between the predicted and measured A-scans, the simulation tool adjusts the material parameters of the object and/or the amplitude of the incident wave pulse to reduce the mismatch. The measure may be the mean square distance between points on the predicted A-scan and the actual A-scan. The user or the simulation tool, or a combination thereof, may select the points to be used in the comparison. Parameter estimation techniques known to those of ordinary skill in the art may be used to adjust the parameters.

The material properties may be provided to the software tool via use input or from a database of properties.

Figure 2:
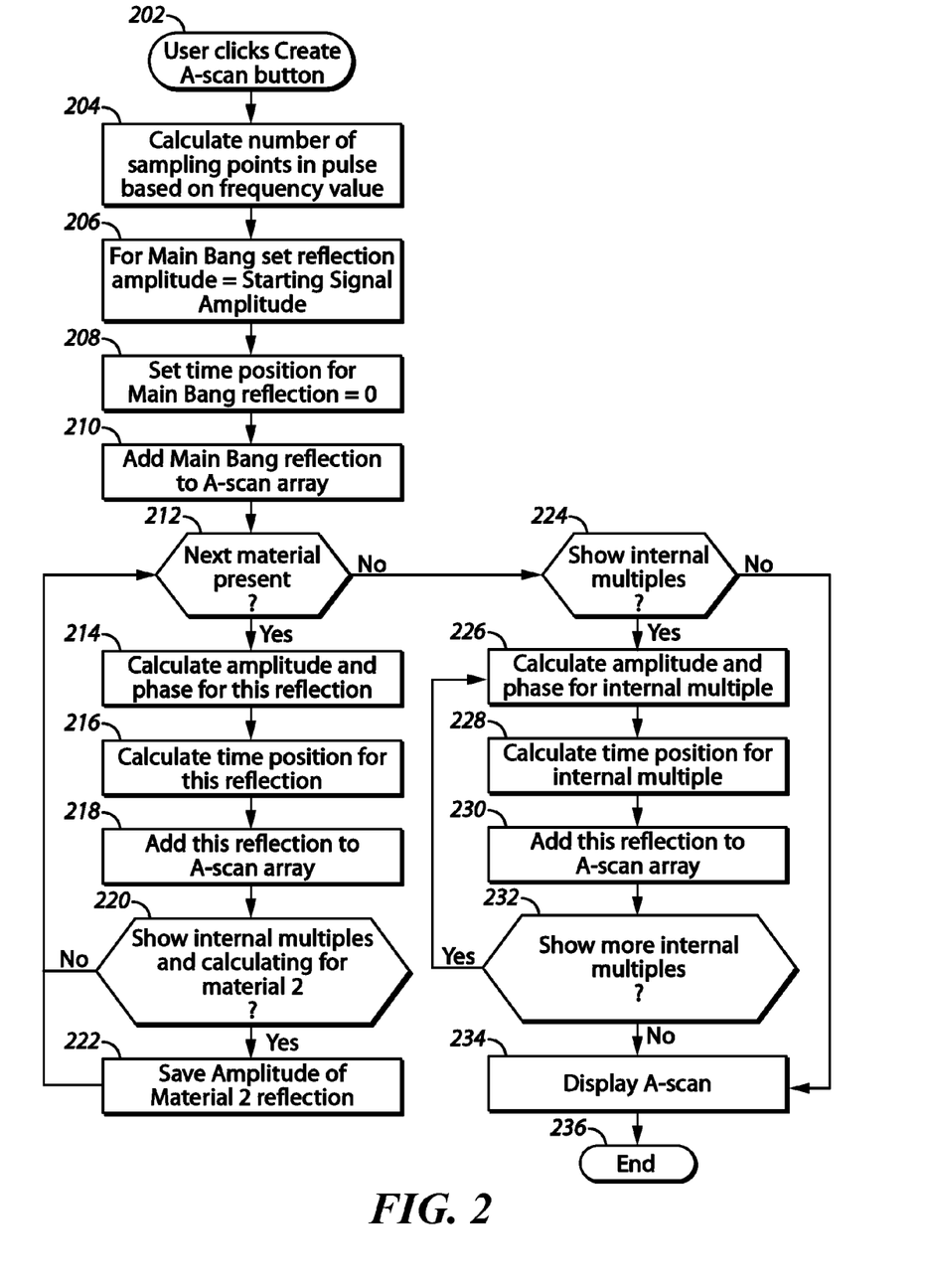
FIG. 2 is a flow chart of a method for a simulation tool to create a predicted A-scan consistent with certain embodiments for the invention.

FIG. 2 is a flow chart of a method for a simulation tool to create a predicted A-scan consistent with certain embodiments for the invention. The process begins, at block 202 in FIG. 2, when the user clicks the button to create an A-scan. At block 204 the number of sampling points in the incident pulse is calculated dependent upon the frequency of the transducer being modeled. At block 206 the starting signal amplitude is set as the received amplitude when the transducer is energized. This signal is termed the main bang response. The time positions of other reflections will be set relative to the time position of the main bang reflection. In this embodiment, the main bang is set to start at time zero at block 208. At block 210, the predicted time history of the main bang response is placed in an A-scan array. At decision block 212, a check is made to determine if more material interfaces are present in the object under inspection. If more material interfaces are present, as depicted by the positive branch from decision block 212, the amplitude and phase for the next reflection is calculated at block 214 and the time position for the reflection is calculated at block 216. At block 218, the reflection is added to the A-scan array.

At decision block 220 a check is made to determine if internal multiples are to be calculated for the interface. If not, as depicted by the negative branch from decision block 220, flow returns to block 212. Otherwise, as depicted by the positive branch from decision block 220, the amplitude and phase of the reflection at the interface is saved (stored) at block 222.

Once reflections for all material interfaces have been calculated, as depicted by the negative branch from decision block 212, a check is made at decision block 224 to determine if internal multiple reflections are to be displayed. If so, as depicted by the positive branch from decision block 224, the amplitude and phase for the next internal multiple is calculated at block 226 and the time position for the reflection is calculated at block 228. At block 230, the reflection is added to the A-scan array. At decision block 232, a check is made to determine if more internal multiples are to be shown. If more internal multiples are to be shown, as depicted by the positive branch from decision block 232, flow returns to block 226. If all internal multiples have been shown, as depicted by the negative branch from decision block 232, or if no internal multiples are to be shown, as depicted by the negative branch from decision block 224, the A-scan is displayed at block 234 and the process terminates at block 236.

The reflected and transmitted (refracted) waves may be calculated using techniques known to those of ordinary skill in the art. One such technique, that simplifies the computation, is to model the incident ultrasonic wave a plane wave. Each interface is characterized by reflection and transmission coefficients that depend upon the relative material properties either side of the interface. Attenuation of the wave as it passes through the coupling medium and the material layers may also be taken into account. In this case, the user interface may be modified to allow the user to enter the estimated attenuation of the material at the selected frequency. Alternatively, the user may select from a list of known materials and the corresponding material parameters may be selected from a database indexed by the material.

Another technique for calculating the reflected and transmitted (refracted) waves is to model a focused wave incident upon the object.

Figure 3:
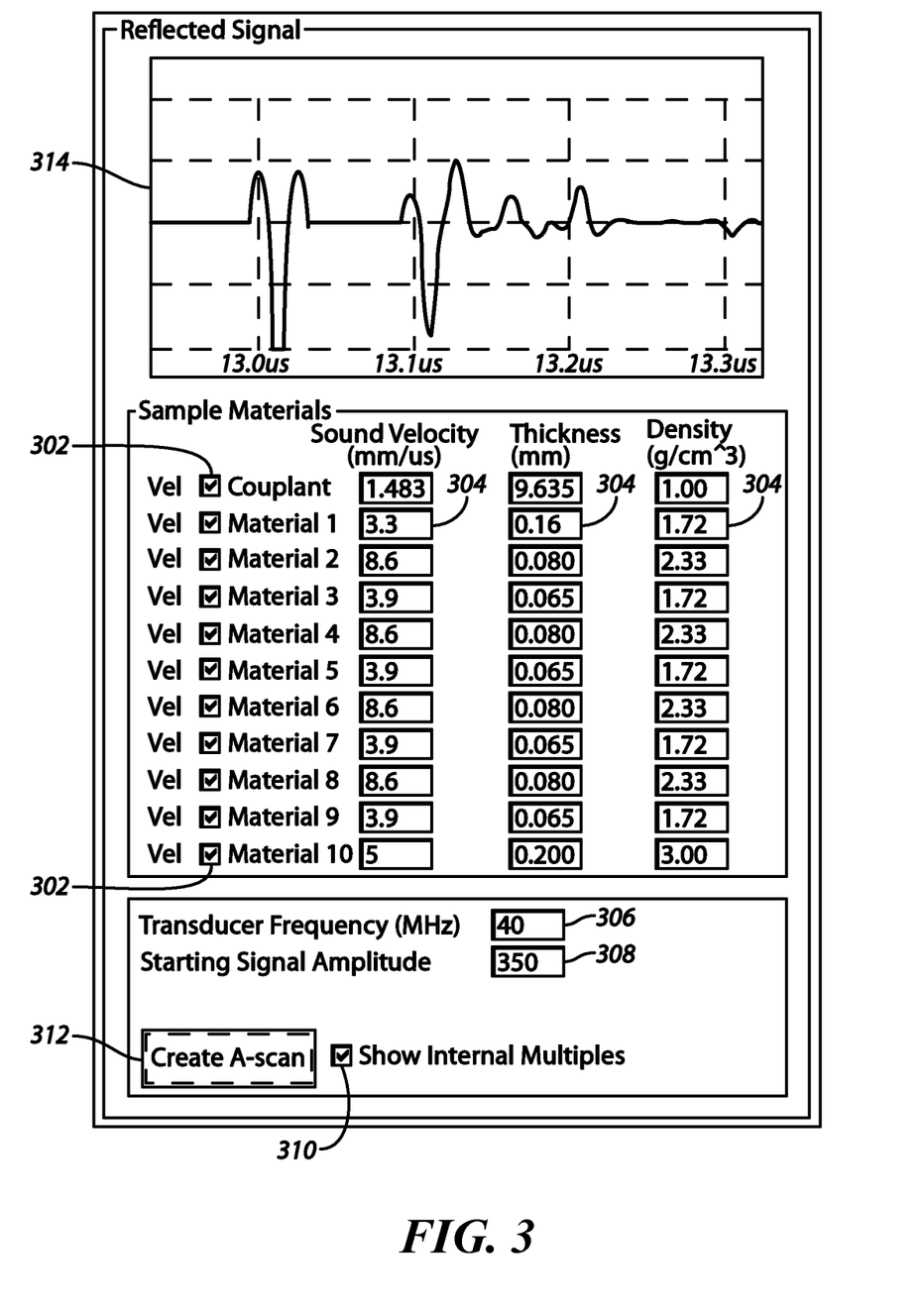
FIG. 3 is an exemplary view of a user interface screen consistent with certain embodiments of the invention.

FIG. 3 is an exemplary view of a user interface screen consistent with certain embodiments of the invention. The screen contains check boxes 302 that enables a user to indicate how many layers are to be modeled, and edit boxes 304 that enables the user to enter the material properties of each layer. Additional edit boxes 306 and 308 allow the user to enter the frequency of the transducer and the starting signal amplitude, respectively. Check box 310 allows the user to indicate whether internal multiples are to be shown in the predicted A-scan. Button 312 allows the user to indicate that the predicted A-scan is to be created and displayed. The predicted A-scan is displayed in graphics box 314.

Figure 4:
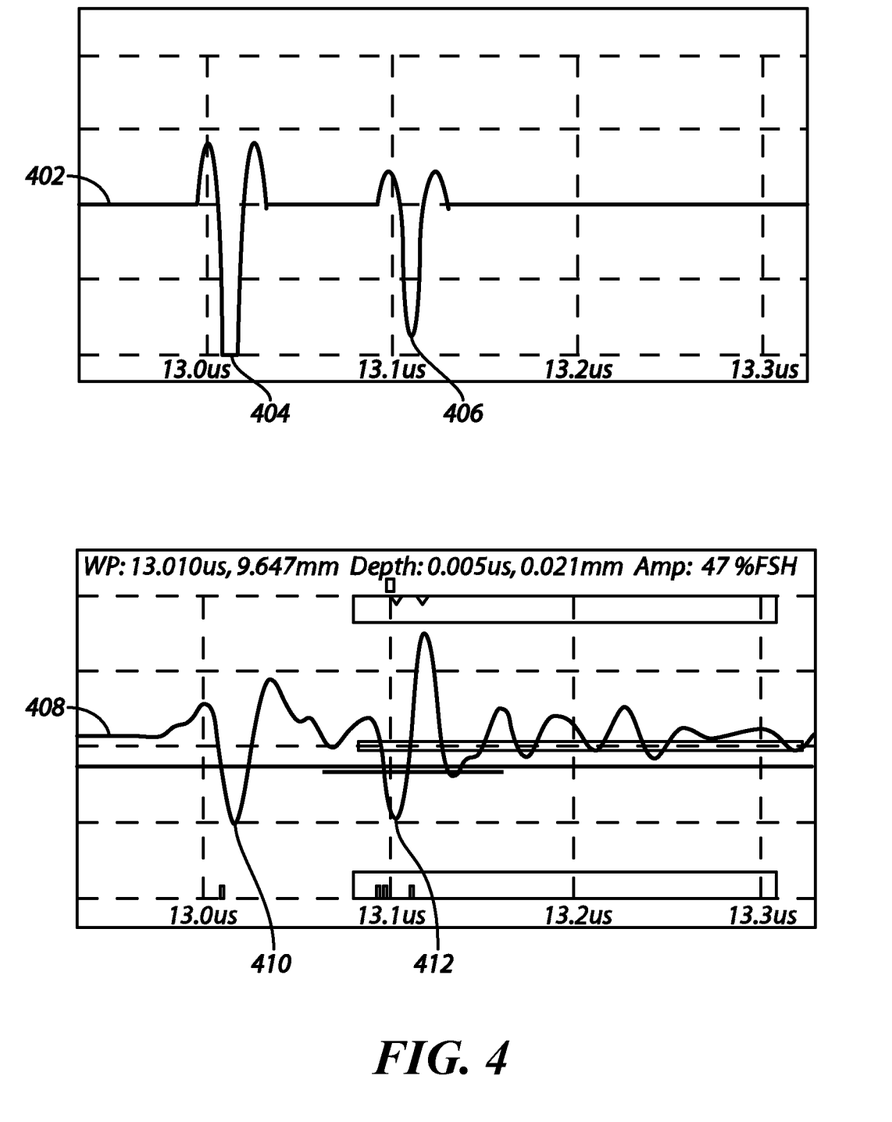
FIGS. 4-7 show comparisons of exemplary predicted and measured A-scans of an object under inspection, illustrative of sequential interface inclusion in the predicted A-scan, consistent with certain embodiments of the invention.

One feature of the software tool is that it allows the user to compare predicted and actual (measured) A-scan waveforms. An example is shown in FIG. 4. In this example, the object under inspection is an electronic component having four silicon die, coupled by epoxy attach layers and encased in a mold compound. Thus the object has a total of nine layers. Referring to FIG. 4, upper plot 402 is a predicted A-scan waveform showing only the reflection 404 from the surface of the object closest to the transducer and the reflection 406 from the internal interface between the upper surface of the top silicon die and the mold compound. The lower plot 408 shows the corresponding negative peaks 410 and 412 in a measured A-scan waveform. This comparison allows the user to adjust the material properties, if desired, to more closely match the features. In addition, it allows the user to correctly identify the negative peak 412 as being the reflection of interest and to set the time gate accordingly.

Figure 5:
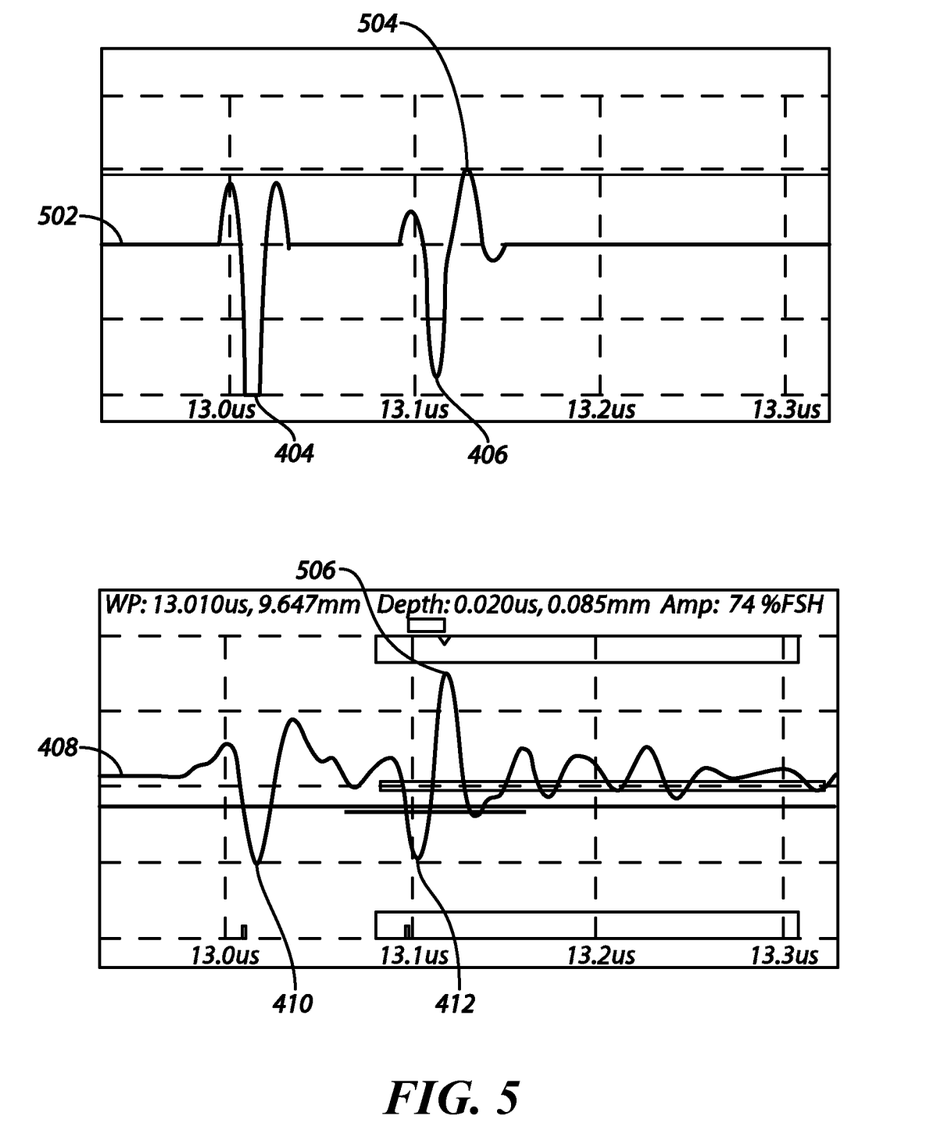
Figure 6:
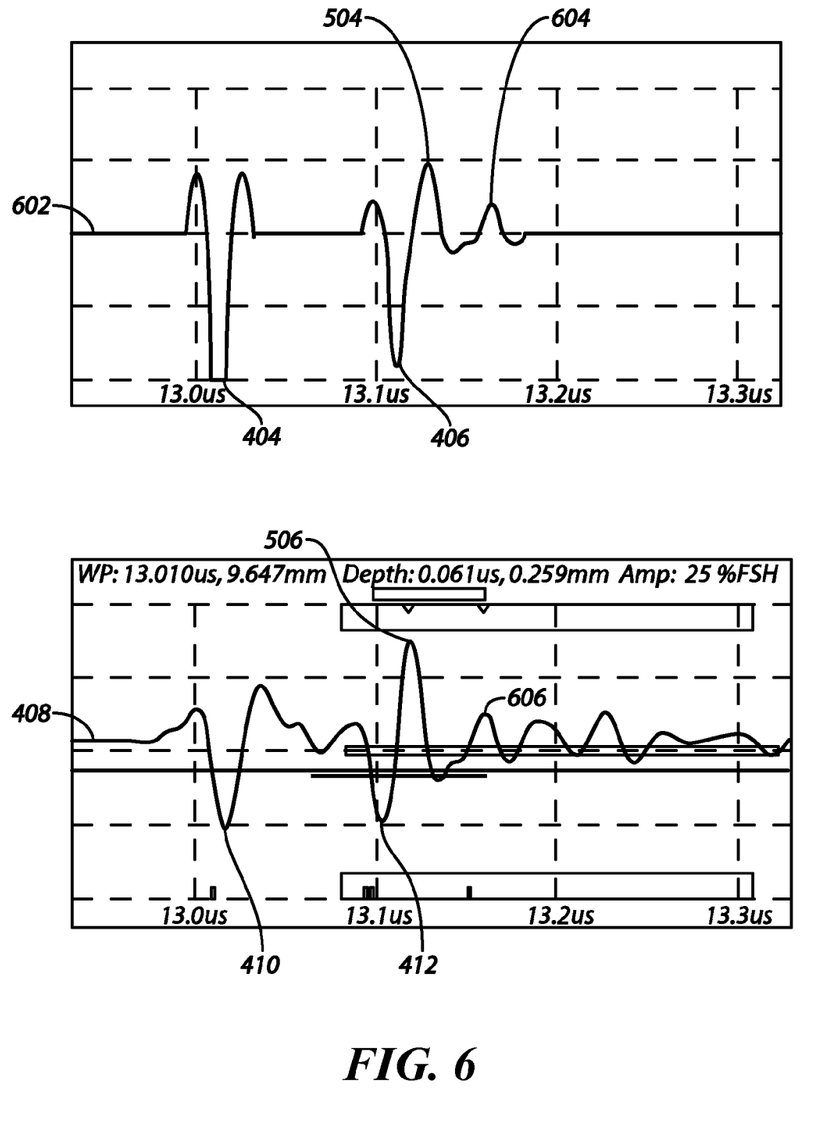
Figure 7:
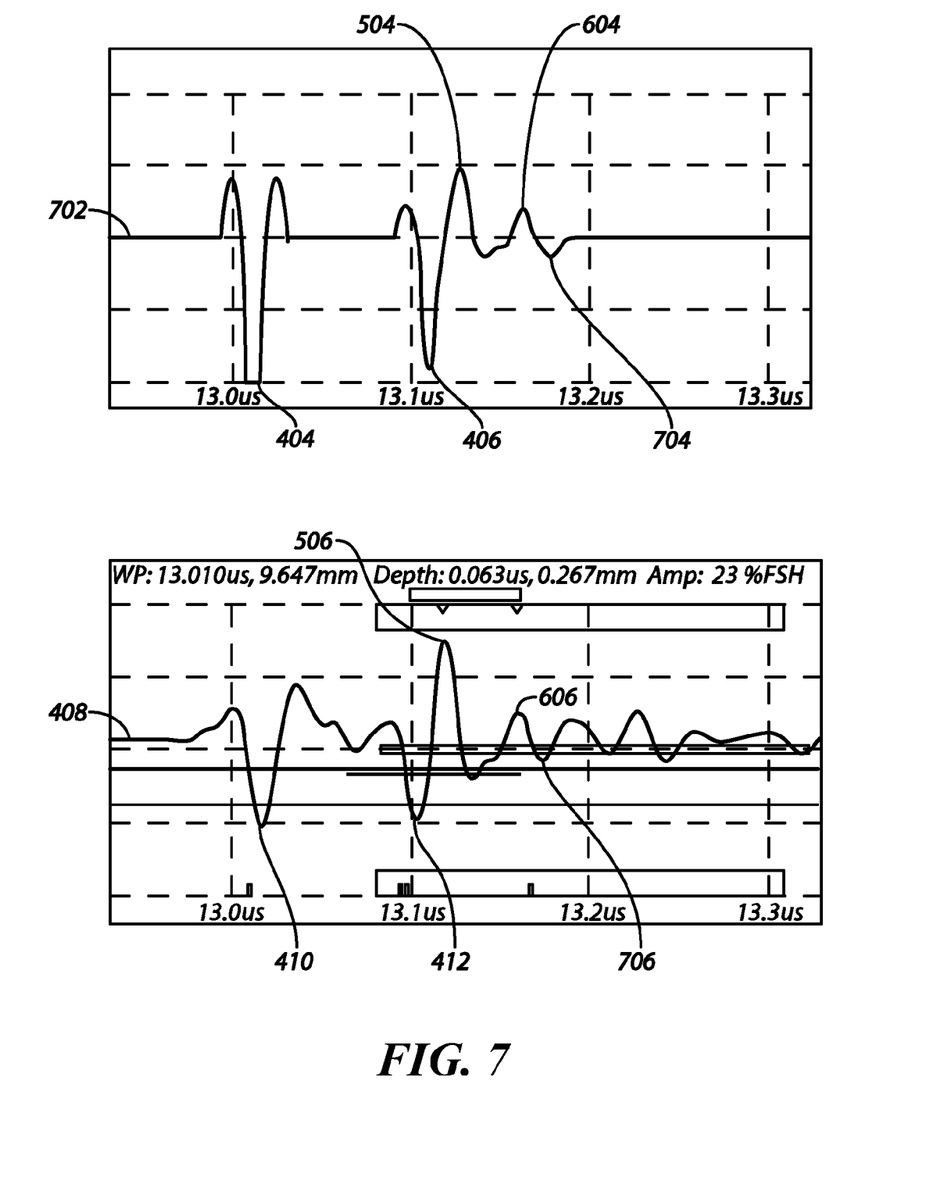

FIGS. 5, 6 and 7 show corresponding plots as more material interfaces are added to the model. FIG. 5 shows the addition of the interface between the silicon layers. The upper plot 502 in FIG. 5 shows a new peak 504 corresponding to the new interface added to the model. The lower plot 408 shows the corresponding peak 506 in the measured waveform. This allows the user to position a time gate to improve inspection of the interface.

Similarly, the upper plot 602 in FIG. 6 shows a new peak 604 corresponding to a third interface added to the model. The lower plot 408 shows the corresponding peak 606 in the measured waveform. This allows the user to position a time gate to improve inspection of the third interface. The upper plot 702 in FIG. 7 shows a new peak 704 corresponding to a fourth interface added to the model. The lower plot 408 shows the corresponding peak 706 in the measured waveform.

The ability to add each reflection in sequence allows the user to position multiple time gates to improve inspection of the interfaces of the object under inspection. In addition, it allows the user to determine if two or more reflections overlap in time. Overlap of reflections is a cause of degradation in the resulting image of the object under inspection.

One application of the tool is the determination of material properties of parts where only a subset of the properties is known or where some properties are only known approximately. In this application, the user may enter the known and approximately known material parameters, such as layer thickness, density and sound speed. The tool then computes and displays the predicted waveform (either a transmitted or reflected wave). Default values may be used for unknown parameters. The user may then interact with the tool via a user interface to adjust the unknown or approximately known parameters.

In some objects under inspection, the number of layers and/or the thickness of the layers may vary across the object. For example, if an object lies predominately in the x-y coordinate plane, the material properties may be specified for different regions of the x-y coordinate plane. For example, a user may specify the x and y coordinates of one corner of a rectangular region, together with the x and y extents of the region. In such applications, the user may select the x and y coordinates for which the A-scan is to be predicted. The selection may be made, for example, by entering the x and y coordinates as numerical values or by using a cursor to select a position in a graphical view of the object.

The material and geometric properties of the object may be stored in a database for future use. The properties identified for a particular object may be used as initial estimated properties for an object of the same or similar type. The properties may be generated automatically from a computer readable specification of the object.

Figure 8:
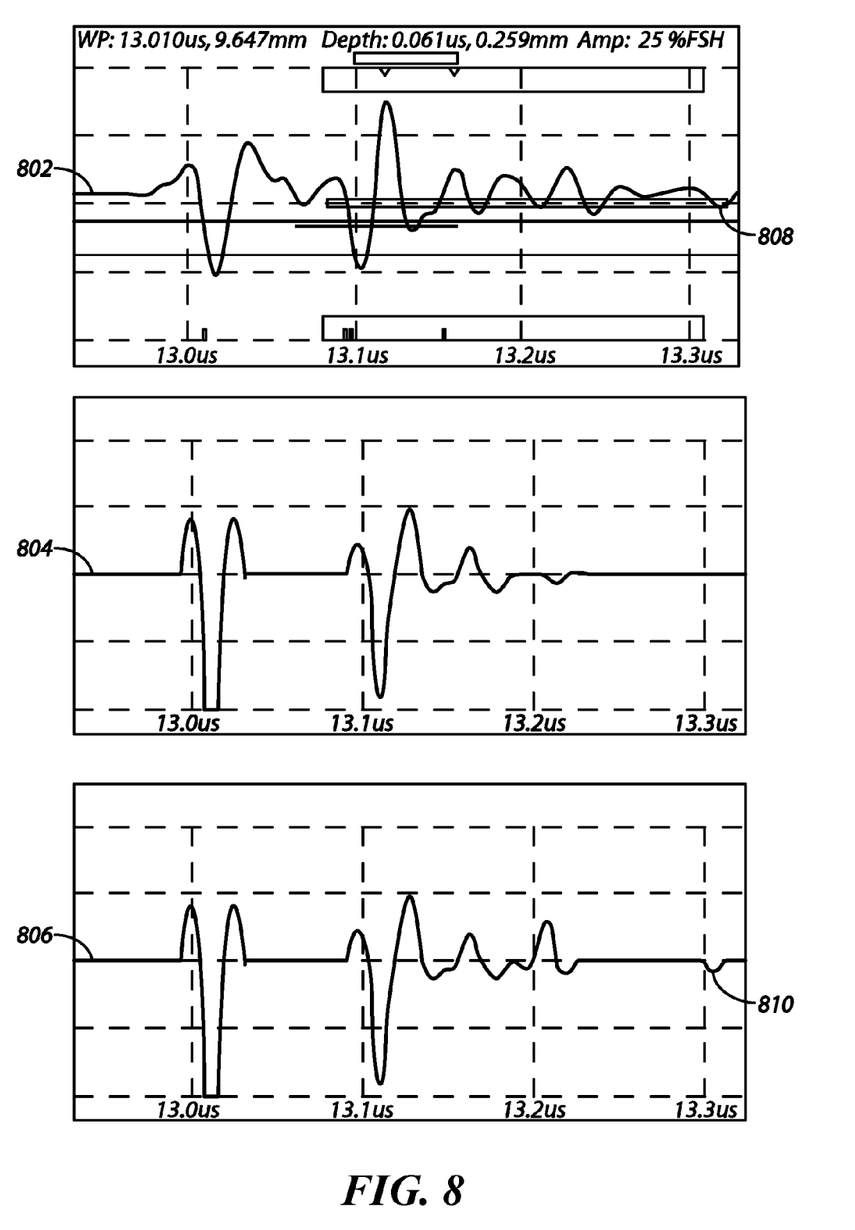
FIG. 8 shows comparison of exemplary predicted and measured A-scans of an object under inspection, illustrative of the inclusion of internal multiples in the predicted A-scan, consistent with certain embodiments of the invention.

FIG. 8 shows a comparison of exemplary predicted and measured A-scans of an object under inspection, illustrative of the inclusion of internal multiples in the predicted A-scan, consistent with certain embodiments of the invention. The top plot 802 in FIG. 8 shows a measured A-scan waveform of a multilayer object. The center plot 804 shows an A-scan waveform predicted using reflections from the layers up to the top of die 3 of the object. The bottom plot 806 shows an A-scan waveform predicted using reflections up to the top of die 3, but also including internal multiples. This inclusion of internal multiple improves the accuracy of the prediction. For example, negative peak 808 in the measured A-scan corresponds to an internal multiple and corresponds to negative peak 810 in the bottom plot. Viewing the predicted A-scan with and without internal multiples allows the user to easily identify the source of features in the A-scan. This allows the user to determine when an internal multiple overlaps and corrupts a primary reflection.

In a further embodiment, the features of the predicted A-scan are labeled or annotated in the display.

In one embodiment, configuring the ultrasonic inspection system comprises predicting a component in the response of the object to ultrasound from the ultrasonic transducer that is due to internal multiples and using the predicted component to reduce the internal multiples in the measured A-scan waveform. For example, the predicted component may be time and amplitude adjusted and then subtracted from the measured A-scan waveform. The measured A-scan with reduced internal multiples may be used to generate scanned images (such as B-scans and C-scans). These scanned images will exhibit less interference from internal multiples. The internal multiples may be reduced in each A-scan as it is measured, or a number of A-scans may be measured and the internal multiples reduced in a post-processing step.

Figure 9:
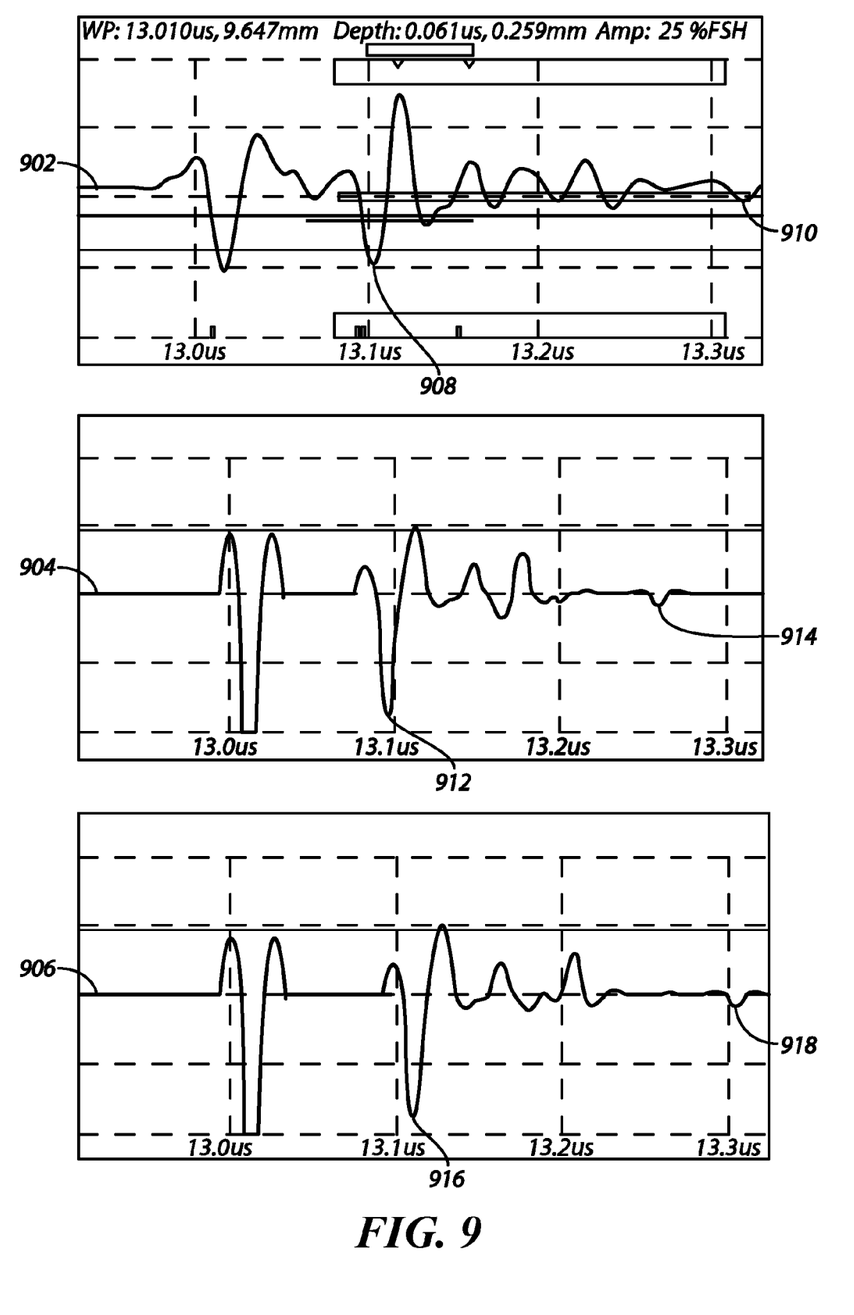
FIG. 9 shows comparison of exemplary predicted and measured A-scans of an object under inspection, illustrative of a method of material characterization consistent with certain embodiments of the invention.

FIG. 9 shows comparison of exemplary predicted and measured A-scans of an object under inspection, illustrative of a method of material characterization consistent with certain embodiments of the invention. In FIG. 9, the top plot 902 shows a measured A-scan waveform of a multilayered object. The center plot 904 shows an A-scan waveform predicted using reflections from the layers up to the top of die 3 of the object. Negative peaks 908 and 910 in plot 902 are not well matched in time by corresponding negative peaks 912 and 914 in plot 904. The prediction was made using an estimated sound speed of 3.9 mm/s in a mold compound in one of the layers of the object. The prediction in the bottom plot 906 was made using an estimated sound speed of 3.3 mm/s in the mold compound. It can be seen that the negative peaks 916 and 918 of plot 906 are better time aligned with the negative peaks 908 and 910, respectively, of plot 902. In one embodiment, the user adjusts the material property (the sound speed in the example above) to improve the time-alignment by entering sound speed values via the user interface. In a further embodiment, the user may indicate which peaks are to be aligned in time, and the alignment is performed automatically by the tool.

Figure 10:
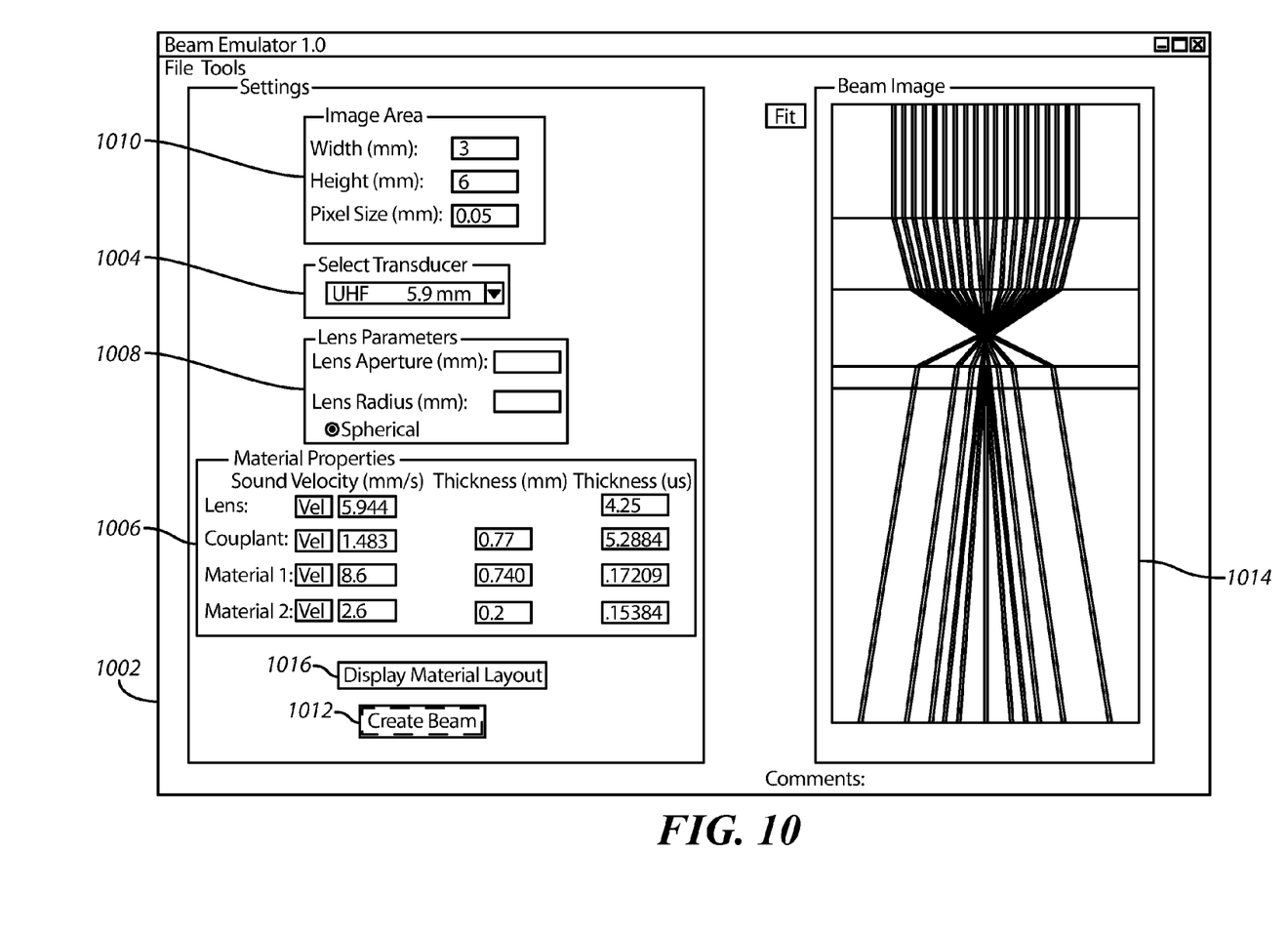
FIG. 10 is an exemplary view of a further user interface screen consistent with certain embodiments of the invention.

FIG. 10 is an exemplary view of a further user interface screen consistent with certain embodiments of the invention. The user interface enables the user of the software tool to enter information so that the software tool can model propagation of an ultrasonic pulse from a transducer through a layered object. Referring to FIG. 10, the user interface 1002 includes a select box 1004 for selecting the type of ultrasonic transducer to be modeled or emulated. The user interface 1002 also includes an area 1006 that enables the user to input material parameters of the propagation media. The propagation media include the layer (or layers if through transmission is be modeled) of couplant media and the material layers of the object under inspection. The media may be characterized by thicknesses and sound speeds, for example. The propagation media may also include an acoustic lens, in which case the user interface may include an additional area 1008 to enable input of lens parameters.

The user interface 1002 also includes an area 1010 that enables the user to input parameters to specify the size and resolution of the cross-section to be displayed. In this example the parameters are entered via edit boxes. However other techniques may be used, such as providing zoom-in and zoom-out buttons.

Button 1012 is pressed to tell the software tool to calculate and display the beam. The calculated beam is displayed in the graphical region 1014. Button 1016 is pressed to tell the software tool to display the material layout in the graphical region.

The path of the beam through a cross-section of the object is shown in the graphical region 1014. The beam may be color-coded or brightness-coded to indicate beam intensity so that the focal region of the beam can be identified easily.

The user may adjust the relative positions of the object under inspection and the transducer by changing the thickness of the couplant layer. This alters the position of the region of focus of the beam and allows the user to select optimal positions for a selected interface. If the beam cannot be focused sufficiently well, the user may select a different transducer and recalculate the beam path. In this manner, the user is able to optimize the configuration of the ultrasonic inspection system by selecting an appropriate transducer and by selecting the relative positions of the transducer and object under inspection to get good focus at an interface of interest.

In one embodiment of the software tool, the predicted spot size and focal zone at a selected interface within the object may be displayed. This further aids the user in the selection and positioning of the ultrasonic transducer.

Those of ordinary skill in the art will recognize that the present invention has been described in terms of exemplary embodiments based upon use of a software tool. However, the invention should not be so limited, since the present invention could be implemented using hardware component equivalents such as special purpose hardware and/or dedicated processors, which are equivalents to the invention as, described and claimed.

The simulation tool may be a stand-alone tool that receives measured ultrasound data as an input, or it may be integrated with an ultrasonic inspection system. In the latter case, the simulation tool may also be operable to configure the ultrasonic inspection system dependent upon the predicted response to an ultrasonic pulse.

Figure 11:
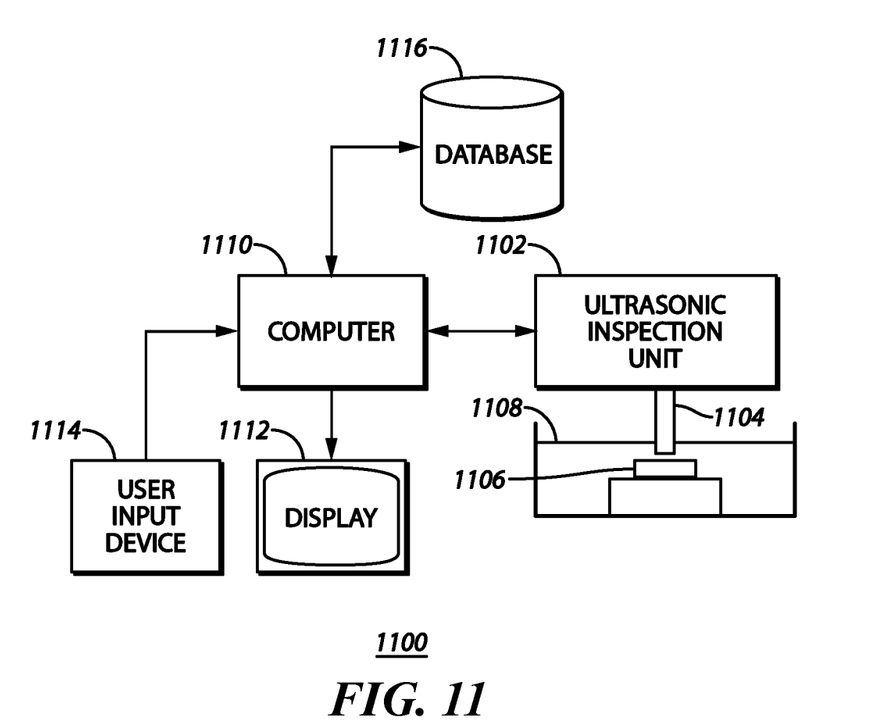
FIG. 11 is a block diagram of an ultrasonic inspection system consistent with certain embodiments of the invention.

FIG. 11 is a block diagram of an exemplary ultrasonic inspection system. The system 1100 includes an ultrasonic inspection unit 1102. This may be, for example, a system for inspecting single parts or an automated system for inspecting multiple parts in a production line. The system may monitor reflected or transmitted ultrasound. An ultrasonic transducer 1104 of the inspection system is used to insonify an object or part 1106. The ultrasonic transducer 1104 may be single element or multiple elements. As is well known to those of ordinary skill in the art, an element may emit or receive ultrasound or both emit and receive ultrasound. Ultrasound from the ultrasonic transducer 1104 is coupled to the object 1106 via a coupling medium or couplant 1108. The couplant may be water, for example, and may be contained in tank as shown or supplied as a fluid flow. The ultrasonic inspection unit 1102 is operable to control the ultrasonic transducer 1104. In particular it may move the transducer to allow for focusing of the ultrasound and scanning of an object. In addition the ultrasonic inspecting unit may be operable to transmit signals to and receive signals from the transducer. The ultrasonic inspection unit 1102 may perform time gating, as described above. A computer or other programmed controller 1110 receives data from the transducer and displays inspection results to the user via graphical display 1112. The computer 1110 receives user input from a user input device 1114. The user input device 1114 may include a keyboard and a computer mouse for example. The graphical display 1112 and user input device 1114 may be combined, as in a touch screen device for example.

In one embodiment, the computer 1110 is operable to configure certain aspects of the ultrasonic inspection unit 1102. For example, the user may select a location on an object to be inspected by moving a cursor over a rendering of the object on the display. The computer may control the position of the ultrasonic transducer such that the corresponding region of the object may be insonified. In a further embodiment the computer 1110 is operable to control the distance between the ultrasonic transducer and the object under inspection so as to adjust the focus of the transducer. The user may select the distance dependent upon a predicted response of the object to the insonification.

In a still further embodiment, the user may select the position of one or more time gates dependent upon a predicted response of the object to the insonification. The selected time gate positions may be communicated from the computer 1110 to the ultrasonic inspection unit 1102.

Database 1116 may be used to stored material properties of known materials. This enables a user to select the material of a layer rather than enter the density and sound speed.

The software tool may be used for interactive user training. The user may define the parameters of simple objects and then view the predicted A-scan (or C-scan) image. The dimensions and orientation of each layer may be entered by the user to create simple objects for which A-scans and C-scans may be generated. This enables the user to learn how surfaces or interfaces affect the resulting A-scan. The user may progress to more complicated objects as understanding increases. The user may adjust the couplant path length to observe the effect of ultrasonic beam focus and select an optimal path length. A cross-sectional view of the object and beam may be displayed to show the beam focal region. The user may adjust the location of the time gate and view corresponding images of an object interface to learn the effects of time gate placement. The user may adjust material characteristics such as density, sound speed and attenuation to observe their effects.

Figure 12:
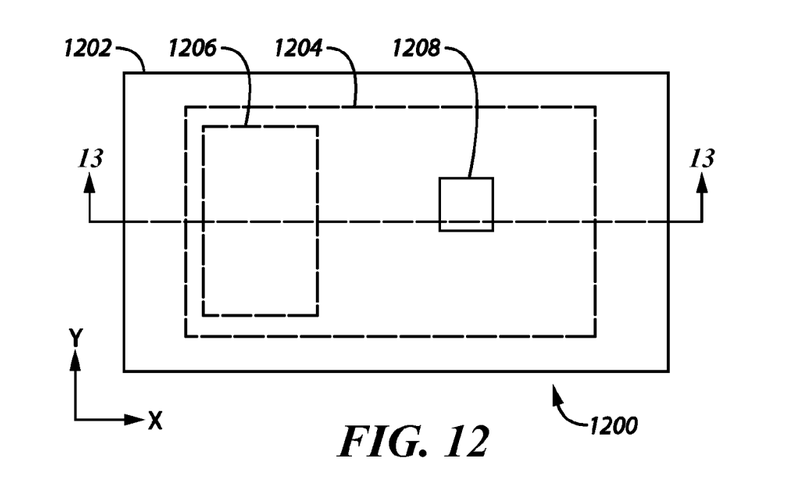
FIG. 12 is a view of an exemplary layered object.

FIG. 12 is a view of an exemplary layered object. The object 1200 has an upper layer 1202, internal layers 1204 and 1206 and a through layer 1208. The object may be specified by the user entering the extent of each layer. The user may then use the software tool to predict A-scans at different positions in the x-y plane, or to predict C-scans of the object for selected time gate positions.

Figure 13:
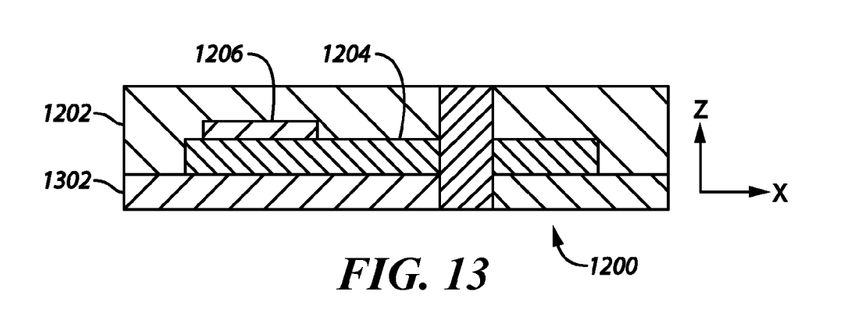
FIG. 13 is a cross-sectional view of the exemplary layered object shown in FIG. 12.

FIG. 13 is a cross-sectional view of the exemplary layered object shown in FIG. 12. The view shows the upper layer 1202, internal layers 1204 and 1206 and a through layer 1208. The object in addition, the view shows a lower layer 1302. The thicknesses and extents of the layers in the z-direction are entered via the user interface of the software tool.

Figure 14:
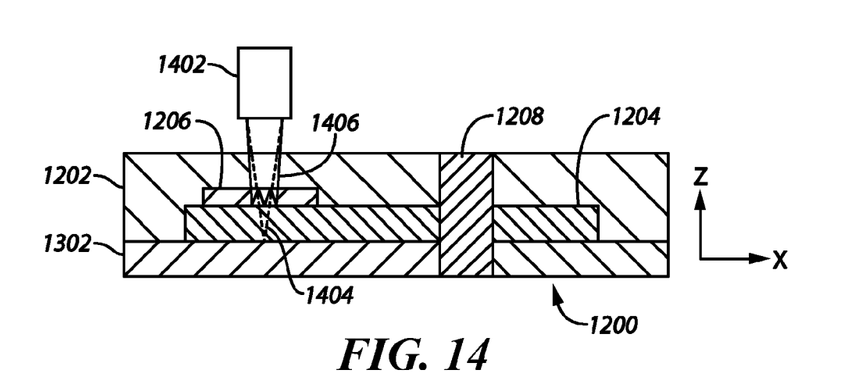
FIG. 14 is a further cross-sectional view of the exemplary layered object shown in FIG. 12.

FIG. 14 is a further cross-sectional view of the exemplary layer object shown in FIG. 12. FIG. 14 shows an ultrasonic transducer 1402 that produces an ultrasonic beam. One path 1404 of the beam is reflected from the interface between layer 1302 and layer 1204 and returns to the transducer 1402. A second path 1406 that includes internal multiples also returns to the transducer. If the sound speeds of layers 1204 and 1206 are similar, the propagation time of each path will be similar and internal multiples from path 1404 will overlap in time with the primary reflection of path 1402. The user will be able to discover this effect while using the software tool.

The software tool may comprise programming instructions stored on a computer readable medium. The programming instructions may be executed on general purpose computers, microprocessor based computers, digital signal processors, microcontrollers, dedicated processors, custom circuits, ASICS and/or dedicated hard wired logic circuits. The programming instructions form program components for creating user interface displays, computing predicted waveforms and generating graphical displays, for example.

Those skilled in the art will appreciate that the programming instructions and associated data used to implement the embodiments described above can be implemented using disc storage as well as other forms of computer readable media, such as, for example, Read Only Memory (ROM) devices, Random Access Memory (RAM) devices, optical storage elements, magnetic storage elements, magneto-optical storage elements, flash memory, core memory and/or other equivalent storage technologies without departing from the present invention. Such alternative storage devices should be considered equivalents.

The present invention, as described in embodiments herein, is implemented using a programmed processor executing programming instructions that are broadly described above in flow chart form that can be stored on any suitable computer readable medium. However, those skilled in the art will appreciate that the processes described above can be implemented in any number of variations and in many suitable programming languages without departing from the present invention. For example, the order of certain operations carried out can often be varied, additional operations can be added or operations can be deleted without departing from the invention. Error trapping can be added and/or enhanced and variations can be made in user interface and information presentation without departing from the present invention. Such variations are contemplated and considered equivalent.

While the invention has been described in conjunction with specific embodiments, it is evident that many alternatives, modifications, permutations and variations will become apparent to those of ordinary skill in the art in light of the foregoing description. Accordingly, it is intended that the present invention embrace all such alternatives, modifications and variations as fall within the scope of the appended claims.

What is claimed is:

1. A computerized method for characterizing properties of an object under inspection by an ultrasonic inspection system, the method comprising:

executing, by a processor, a software simulation tool to predict an ultrasonic wave scattered by the object under inspection from estimated properties of the object under inspection;

measuring an ultrasonic wave scattered by the object under inspection by the ultrasonic inspection system;

enabling a comparison of the predicted ultrasonic wave with the measured ultrasonic wave by:

displaying the predicted ultrasonic wave to a user of the software simulation tool; and displaying the measured ultrasonic wave to the user of the software simulation tool;

responsive to user input, adjusting the estimated properties to improve the degree of match between the predicted ultrasonic wave and the measured ultrasonic wave; and generating an output dependent upon the adjusted estimated properties.

2. A method in accordance with claim 1, wherein the object under inspection comprises a plurality of layers and wherein the properties of the object under inspection comprise the thickness of layers, the sound speed of the layers and the density of the layers.

3. A method in accordance with claim 1, wherein the object under inspection comprises a plurality of layers and wherein the properties of the object under inspection comprise the thickness of layers and the acoustic impedance of the layers.

4. A method in accordance with claim 1, wherein the properties of the object under inspection comprises the attenuation rate of ultrasound in the object under inspection.

5. A method in accordance with claim 1, wherein adjusting the estimated properties to improve the degree of match between the predicted ultrasonic wave and the measured ultrasonic wave comprises adjusting the estimated properties in response to the user of the software simulation tool inputting at least one new estimated property of the object.

6. A method in accordance with claim 1, wherein executing the software simulation tool to predict the ultrasonic wave scattered by the object under inspection from estimated properties of the object under inspection is responsive to the user of the software simulation tool selecting the estimated properties of the object via a user interface.

7. A method in accordance with claim 1, wherein predicting an ultrasonic wave, comparing the predicted ultrasonic wave with the measured ultrasonic wave and adjusting the estimated properties to improve the match between the predicted ultrasonic wave and the measured ultrasonic wave are performed by the software simulation tool.

8. A system for characterizing properties of an object under inspection, the system comprising:

a processor operable to execute a software simulation tool to predict an ultrasonic wave scattered by the object under inspection from estimated properties of the object;

an ultrasonic inspection system operable to measure an ultrasonic wave scattered by the object under inspection;

a display coupled to the processor and operable to display the predicted ultrasonic wave and the measured ultrasonic wave to a user of the software simulation tool; and a user input device operable to receive user input;

wherein the system is operable to adjust the estimated properties of the object in response to the user input to improve the degree of match between the predicted ultrasonic wave and the measured ultrasonic wave.

9. The system of claim 8, wherein the software simulation tool of the system is operable to compare the predicted ultrasonic wave with the measured ultrasonic wave.

10. A non-transitory computer readable medium containing program instructions that, when executed on a processor, characterize properties of an object under ultrasonic inspection by:

a software simulation tool executed on the processor predicting an ultrasonic wave scattered by the object under inspection from estimated properties of the object:

measuring an ultrasonic wave scattered by the object under inspection on an ultrasonic inspection system;

enabling a comparison of the predicted ultrasonic wave with the measured ultrasonic wave by:
displaying the predicted ultrasonic wave to a user of the software simulation tool; and
displaying the measured ultrasonic wave to the user of the software simulation tool; and responsive to user input, adjusting the estimated properties to improve the degree of match between the predicted ultrasonic wave and the measured ultrasonic wave.

11. A method in accordance with claim 1, wherein the object under inspection comprises a plurality of layers, wherein the estimated properties of the object under inspection comprise the thicknesses of the layers and acoustic properties of the layers, and wherein executing the software simulation tool on the processor to predict the ultrasonic wave scattered comprises predicting reflections of the ultrasonic wave at one or more material interface in the object under inspection.

12. A method in accordance with claim 1, wherein generating an output comprises determining configuration properties of the ultrasonic inspection system dependent upon the adjusted estimated properties, the configuration properties comprising one or more of:

a position of a time gate;

an ultrasonic transducer selection; and a position of an ultrasonic transducer to achieve good focus.

13. A method in accordance with claim 1, further comprising:

presenting a first user interface to the user to enable the user to enter the estimated properties of the object to be inspected; and presenting a second user interface to the user to enable the user to enter at least one property of an ultrasonic transducer, wherein the software simulation tool is responsive to the estimated properties of the object to be inspected and the at least one property of an ultrasonic transducer.

14. A system in accordance with claim 8, wherein the object under inspection comprises a plurality of layers, wherein the estimated properties of the object under inspection comprise the thicknesses of the layers, and acoustic properties of the layers, and wherein the software simulation tool is operable to predict reflections of the ultrasonic wave at one or more material interface in the object under inspection.

15. A system in accordance with claim 8, wherein a configuration of the ultrasonic inspection system is determined dependent upon the adjusted estimated properties of the object under inspection, the configuration comprising one or more of:

a position of a time gate;

an ultrasonic transducer selection; and a position of an ultrasonic transducer to achieve good focus.

16. A non-transitory medium in accordance with claim 10, wherein the object under inspection comprises a plurality of layers, wherein the estimated properties of the object under inspection comprise the thicknesses of the layers, and acoustic properties of the layers, and wherein the software simulation tool predicting the ultrasonic wave scattered by the object under inspection comprises the software simulation tool predicting reflections of the ultrasonic wave at one or more material interface in the object under inspection.

\* \* \* \* \*